(12) United States Patent
Dal Negro et al.

(10) Patent No.: US 7,903,246 B2
(45) Date of Patent: Mar. 8, 2011

(54) DETERMINISTIC APERIODIC PATTERNED DIELECTRIC AND PLASMONIC MATERIALS FOR LOCALIZED ELECTROMAGNETIC FIELD ENHANCEMENT

(75) Inventors: Luca Dal Negro, Cambridge, MA (US); Ashwin Gopinath, Boston, MA (US); Ning-Ning Feng, Somerville, MA (US); Mark Luitzen Brongersma, Redwood City, CA (US)

(73) Assignees: Trustees of Boston University, Boston, MA (US); The Board of Trustees of the Leland Stanford Junior University, Palo Alto, CA (US)

( * ) Notice: Subject to any disclaimer, the term of this patent is extended or adjusted under 35 U.S.C. 154(b) by 137 days.

(21) Appl. No.: 12/423,508

(22) Filed: Apr. 14, 2009

(65) Prior Publication Data

US 2009/0195879 A1 Aug. 6, 2009

Related U.S. Application Data

(63) Continuation of application No. PCT/US2007/083140, filed on Oct. 31, 2007.

(60) Provisional application No. 60/855,543, filed on Oct. 31, 2006.

(51) Int. Cl.
*G01J 3/44* (2006.01)
*G01N 21/65* (2006.01)
(52) U.S. Cl. .......................................... 356/301; 356/244
(58) Field of Classification Search .................. 356/301
See application file for complete search history.

(56) References Cited

U.S. PATENT DOCUMENTS

2004/0086249 A1 5/2004 Zoorob
2005/0094277 A1 5/2005 Khusnatdinov et al.

OTHER PUBLICATIONS

Albuquerque et al., Theory of elementary excitations in quasiperiodic structures, Physics Reports, vol. 376, Issues 4-5, Mar. 2003, pp. 225-337.*
Dulea et al., "Transmission of Light Through Deterministic Aperiodic Non-Fibonaccian Multilayers," Physical Review B, vol. 42, No. 6, Aug. 15, 1990, pp. 3680-3689.

(Continued)

*Primary Examiner* — F. L Evans
(74) *Attorney, Agent, or Firm* — BainwoodHuang

(57) ABSTRACT

A method is shown for the extension in higher spatial dimensions of deterministic, aperiodic structures which exhibit strong aperiodic effects and have overall compatibility with the planar technology of integrated optical circuits. Disclosed devices are operative in response to incident electromagnetic energy to create a distribution of electromagnetic energy having localized electromagnetic field enhancement, wherein the device includes a dielectric or plasmonic material having a region of interaction with the incident electromagnetic energy. The region of interaction has a deterministic, aperiodic patterning with an array of individual patterning elements of distinct refractive indices such that a variation of refractive index of the device occurs over distances comparable with a wavelength of the incident electromagnetic energy, the array being a multi-dimensional extension of a corresponding one-dimensional sequence such that a spectral response of the array is a multi-dimensional equivalent of a spectral response of the one-dimensional sequence. Specific examples employing so-called Rudin-Shapiro, Thue-Morse and Fibonacci sequences are shown.

11 Claims, 7 Drawing Sheets

OTHER PUBLICATIONS

Galdi et al., "Radiation Properties of One-Dimensional Random-Like Antenna Arrays Based on Rudin-Shapiro Sequences," IEEE Transactions on Antennas and Propagation, vol. 53, No. 11, Nov. 2005, pp. 3568-3575.

Sanchez et al., "Application of Renormalization and Convolution Methods to the Kubo-Greenwood Formula in Multidimensional Fibonacci Systems," Physical Review B, vol. 70, No. 14, Oct. 29, 2004, pp. 144207-1-144207-12.

Yang et al., "Fabrication of Two-Dimensional Metallodielectric Quasicrystals by Single-Beam Holography," Applied Physics Letters, vol. 88, No. 25, Jun. 20, 2006, p. 251104-1-251104-3.

Zhang et al., "Growth and Characterization of GaAs/AlGaAs Thue-Morse Quasicrystal Photonic Bandgap Structures," Chinese Physics Letters, vol. 22, No. 5, 2005, pp. 1191-1194.

International Search Report and Written Opinion from PCT/US2007/083140, mailed on Jun. 6, 2008.

* cited by examiner

DETERMINISTIC APERIODIC PATTERNED DIELECTRIC AND PLASMONIC MATERIALS FOR LOCALIZED ELECTROMAGNETIC FIELD ENHANCEMENT

BACKGROUND

The control of light-matter interaction in complex dielectrics without translational invariance offers great potential for the creation and manipulation of light states.

Complex dielectrics are dielectric structures in which the refractive index varies over length scales comparable to the wavelength of light. In disordered materials, light waves undergo a multiple scattering process and are subject to interference effects leading to Anderson light localization. One of the first phenomena studied in this context was coherent backscattering or weak localization of light. Multiple light scattering in disordered dielectrics shows many similarities with the propagation of electrons in semiconductors, and various phenomena that are known for electron transport also appear to have their counterpart in optics. Important examples are the optical Hall effect and optical magnetoresistance, universal conductance fluctuations of light waves, optical negative temperature coefficient resistance, and Anderson localization of light.

Also known are periodic dielectric structures which behave as semiconductor crystals for light waves. In periodic structures, the interference is constructive in well-defined propagation directions, which leads to Bragg scattering and complete reflection. At high enough refractive index contrast, propagation is prohibited in any direction within a characteristic range of frequencies. This phenomenon is referred to as a photonic band gap in analogy with the electronic band gap in a semiconductor.

For example, so-called "quasicrystals" are nonperiodic structures that are constructed following a simple deterministic generation rule. If made from dielectric material, the resulting structure has fascinating optical properties. Quasicrystals of the Fibonacci type, for instance, exhibit an energy spectrum with pseudo band gaps and separate areas of high field localization. A Fibonacci quasicrystal is a deterministic aperiodic structure that is formed by stacking two different compounds (referred to as A and B) according to a Fibonacci generation scheme: $S_{j+1}=\{S_{j-1}S_j\}$ for $j>=1$, with $S_0=\{B\}$ and $S_1=\{A\}$. The lower order sequences are $S_2=\{BA\}$, $S_3=\{ABA\}$, $S_4=\{BAABA\}$, etc.

SUMMARY

In devices such as quasicrystals employing one dimensional multilayer stacks, the total number of layers is limited by layer thickness control, stress relaxation and cracking, compromising the sample regularity through uncontrollable thickness and refractive index variations. Therefore alternative approaches for the generation of large-size, regular and higher-dimensional structures are needed in order to enable the fabrication of novel optical devices based on the concept of aperiodic order.

A method is disclosed for the extension in higher spatial dimensions of deterministic, aperiodic structures which exhibit strong aperiodic effects and have overall compatibility with the planar technology of integrated optical circuits. Disclosed devices are operative in response to incident electromagnetic energy to create a distribution of electromagnetic energy having localized electromagnetic field enhancement, wherein the device includes a dielectric or plasmonic (metal) material having a region of interaction with the incident electromagnetic energy. The region of interaction has a deterministic, aperiodic patterning with an array of individual patterning elements of distinct refractive indices such that a variation of refractive index of the device occurs over distances comparable or smaller than the wavelength of the incident electromagnetic energy, the array being a multi-dimensional extension of a corresponding one-dimensional sequence such that a spectral response of the array is a multi-dimensional equivalent of a spectral response of the one-dimensional sequence. Specific examples are shown employing so-called Rudin-Shapiro, Thue-Morse and Fibonacci sequences, which are the chief examples of the three main classes of deterministic aperiodic sequences characterized by absolutely continuous, singular continuous and quasi-periodic Fourier spectra respectively.

The strategy for the extension of optical devices to two and three dimensions enables the control of novel optical functions, akin to the complex optical response of random media, in deterministically generated optical chips which can be fabricated with the standard toolsets of the microelectronics industry. In particular, giant electric field enhancement effects and fractal resonances, hot electromagnetic spots in metal/dielectric structures and dramatic group velocity dispersion (GVD) effects could all be engineered onto well-reproducible device structures possessing a high degree of structural complexity.

The degree of light localization and the associated field enhancement effects in the two- and three-dimensional generalizations of aperiodic optical structures have a large potential for a variety of optical device applications. In particular, it is believed that the extension of aperiodic order to higher dimensional structures will have an impact in the following fields of applications:

Surface-enhanced Raman spectroscopy (SERS)
Single molecule detection
Efficient extraction in light emitting diodes (LEDs)
2D and 3D fractal lasers
Input/output plasmonics couplers

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Figure 1:
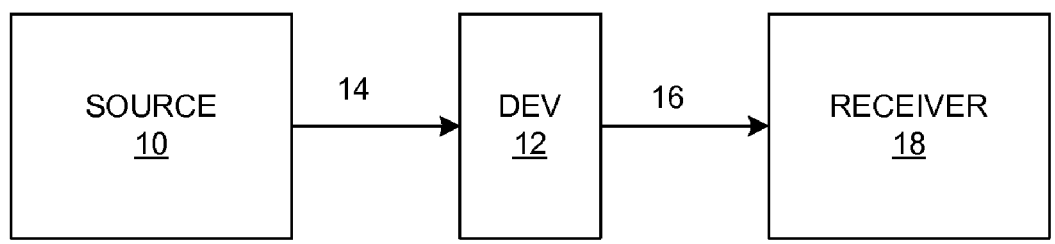
FIG. 1 is a general block diagram of a system utilizing a device employing deterministic, aperiodic patterning in accordance with an embodiment of the invention.

FIG. 1 is a general block diagram of a system. A source 10 generates source electromagnetic energy such as light and directs it to a device 12 in the form of incident electromagnetic energy 14. The incident electromagnetic energy 14 interacts with the device 12 in a desired fashion, and resulting electromagnetic energy 16 from this interaction is directed to a receiver 18. In many cases the interaction employs reflection (such as from a two-dimensional surface in device 12), but alternative embodiments may employ transmission. The receiver 18 typically processes the resulting electromagnetic energy 16 to achieve some system-related purpose, examples of which are provided below.

The device 12 employs deterministic, aperiodic patterning with an array of individual patterning elements of distinct refractive indices such that a variation of refractive index of the device occurs over distances comparable with a wavelength of the incident electromagnetic energy 14. The array is a multi-dimensional extension of a corresponding one-dimensional sequence, such that a spectral response (or Fourier characteristics) of the array is a multi-dimensional equivalent of a spectral response of the one-dimensional sequence. Described herein are devices and methods based on the successive iteration of defining inflation rules along the different spatial directions (e.g., row and columns) of an appropriate symbolic matrix. This procedure guarantees the complete extensions of the Fourier properties of one-dimensional non-periodic sequences to higher dimensions. This method enables the fabrication of planar (or even three-dimensional) optical devices 12 with arbitrary light transport properties, ranging from perfectly ballistic to Anderson localized transport on a deterministic chip.

To briefly describe the generation method, let $f_a$ be the inflation rule which generates a non-periodic (quasi-periodic and aperiodic) structure along a given direction 'a'. This means that upon the action of $f_a$ on a letter alphabet (a set of symbols), every symbol in the sequence is expanded in the 'a' direction as prescribed by the inflation rule. The successive iterations of $f_a$ results in a deterministically generated one-dimensional symbolic sequence. In order to generalize non-periodic sequences in higher dimensional spaces, the application of one-dimensional inflation rules is alternated along different spatial dimensions, operating on non-periodic symbolic matrices as described in the following.

Consider the extension of a one-dimensional aperiodic sequence into two dimensions. This can be done conveniently by defining symbolically a 2D inflation as:

$$f_{xy} = f_y(f_x)$$

which first acts upon an arbitrary x direction and subsequently upon the perpendicular y direction. Successive applications of the 2D inflation procedure will give all the orders of the aperiodic 2D sequence as:

$$f^{(1)}_{xy} = f_y(f_x(X)), \quad (1^{st}\ \text{order})$$

$$f^{(2)}_{xy} = f_y(f_x(f^{(1)}_{xy})), \quad (2^{nd}\ \text{order})$$

$$f^{(3)}_{xy} = f_y(f_x(f^{(2)}_{xy})), \quad (3^{rd}\ \text{order})$$

.

.

.

$$f^{(n)}_{xy} = f_y(f_x(f^{(n-1)}_{xy})) \quad (N^{th}\ \text{order})$$

In the above description, X is the seed term upon which the inflation acts, and n is the generation number of the structure. A typical device 12 will employ a patterning using an appropriate order based in part on the overall size of the device versus the size granularity of the patterning. For example, if the device 12 has a width of 10 um and employs pattern elements of size 50 nm, it will have about 200 pattern elements across its width, and thus an order of the sequence is chosen that has 200 or more individual elements. In many cases, a sequence of order 8 might be appropriate in such a circumstances.

Several examples of the device 12 are described below, along with the corresponding defining inflation rules and spectral characteristics.

Figure 2:
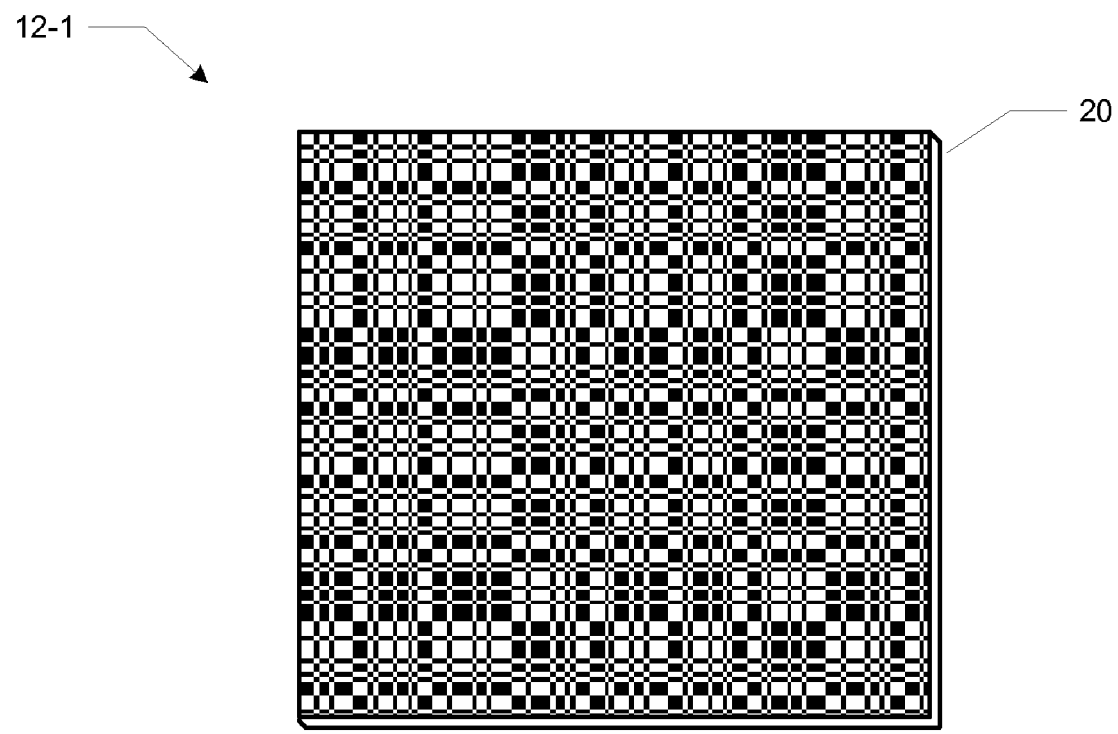
FIG. 2 is a diagram showing the patterning of a device according to a first embodiment based on a Rudin-Shapiro (RS) sequence.

FIG. 2 shows an example of a device 12-1 employing a first type of defining inflation rule, which is based on the known Rudin-Shapiro sequence. As shown, the device 12-1 includes a substrate 20 of dielectric or "plasmonic" material with binary patterning on one surface. Here "plasmonic" refers to the ability of the substrate 20 to exhibit plasmon excitation, and typical materials are metals such as gold or silver film. The binary patterning can be accomplished by deposition techniques, such as deposition of discrete nanoparticles having a dielectric constant differing from that of the material of the substrate 20, or by etching or other surface processing that creates the desired binary contour.

The Rudin-Shapiro one dimensional sequence $f_{RS}$ (x is created by following the two-letter inflation rule:

AA ⟶ AAAB
AB ⟶ AABA
BA ⟶ BBAB
BB ⟶ BBBA

Unlike other sequences such as discussed below, the inflation rule for RS acts upon two-letters combinations as opposed to only one letter. One method for the generalization to higher dimensions can be applied by inflating starting from a 2×2 seed matrix, as shown below. A two-dimensional extension of the Rudin-Shapiro sequence (the n×n RS matrix) can be obtained by the application of the following inflation scheme:

The first inflation steps are as follows:

$$\begin{matrix} BA \\ AB \end{matrix} \xrightarrow{f_{RS}(x)} \begin{matrix} BBAB \\ AABA \end{matrix} \xrightarrow{f_{RS}(y)} \begin{matrix} BBAB \\ BBAB \\ AABA \\ BBAB \end{matrix}$$

In the above, the seed on the left is the $1^{st}$ order term, and the term of size 4×4 on the right is the $2^{nd}$ order term. By iteration of the above procedure the desired 2D generalization of the aperiodic Rudin-Shapiro sequence is obtained. FIG. 2 shows the sixth-order term of this sequence, with the light and dark squares corresponding to the "B" and "A" symbols respectively.

Figure 3:
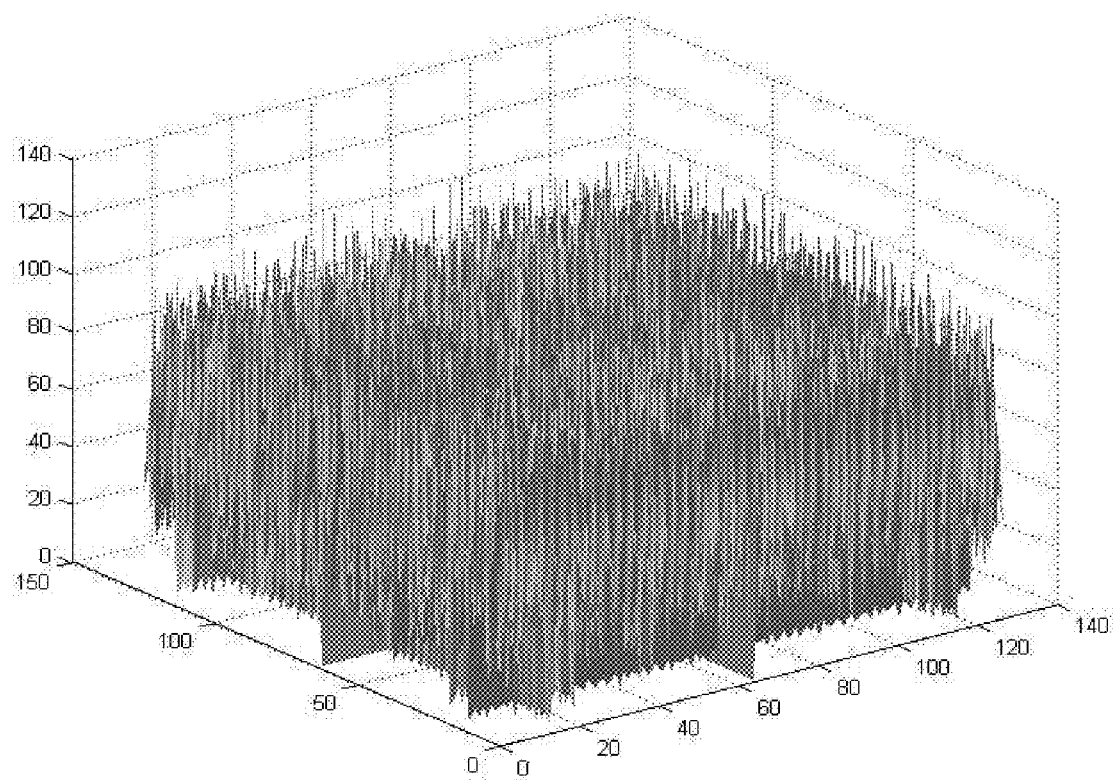
FIG. 3 is a plot of the two-dimensional spectrum of the RS device of FIG. 2.
Figure 4:
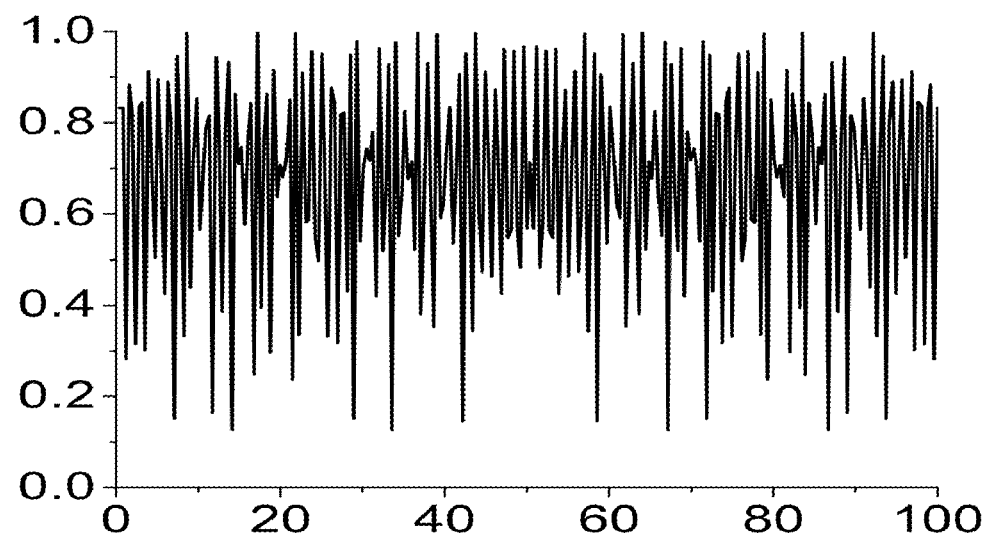
FIG. 4 is a plot of the spectrum of a one-dimensional RS sequence.
Figure 5:
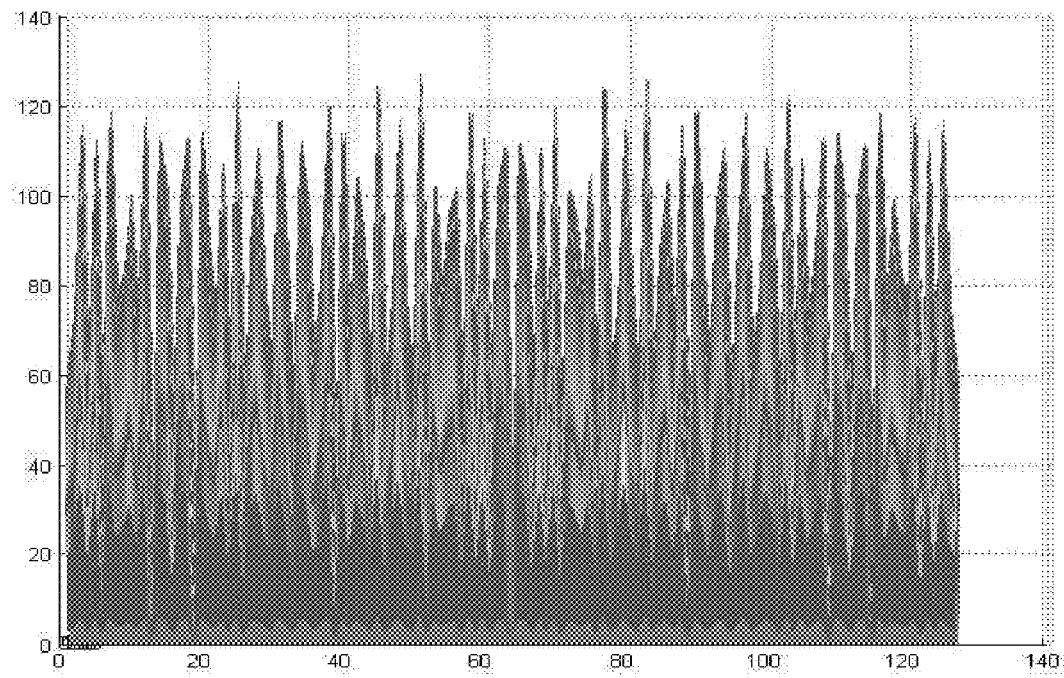
FIG. 5 is a plot of a single vertical slice of the two-dimensional spectrum of FIG. 3.

FIG. 3 shows the two-dimensional Fourier spectrum of the RS device 12-1. It will be observed that this spectrum is highly uniform in amplitude across its range. Additionally, the 2D spectrum retains the spectral characteristics of the 1-D RS sequence, as can be appreciated by referring to FIGS. 4 and 5. FIG. 4 shows the Fourier spectrum of the one-dimensional RS sequence, and FIG. 5 shows a "slice" of the 2D spectrum of FIG. 3 along one vertical plane. They are substantially identical. Thus, the Fourier characteristics of the one-dimensional RS sequence have been extended into two dimensions. A two-dimensional aperiodic device having a continuous Fourier spectrum (a chief property of RS structures) has been deterministically created.

Figure 6:
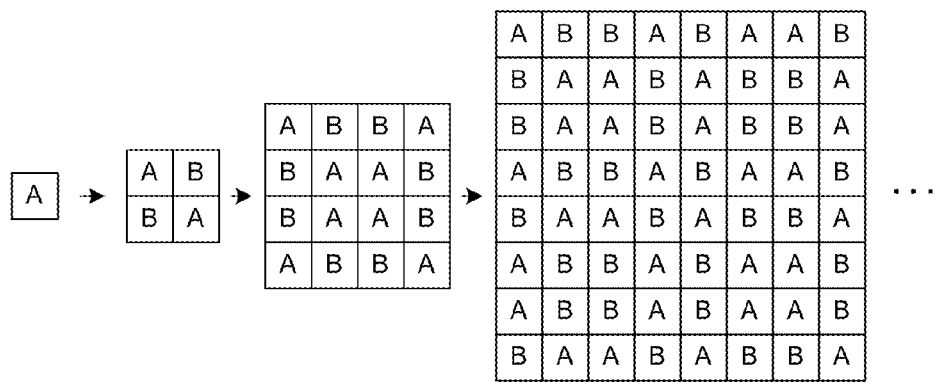
FIG. 6 is a diagram illustrating the inflation rules for arriving at a patterning of a device according to a second embodiment based on a Thue-Morse (TM) sequence.

FIG. 6 illustrates an example of an alternative two-dimensional inflation rule that may be employed to arrive at a 2D pattern for the device 12. The illustrated rule is based on so-called "Thue-Morse" sequences. The standard one-dimensional Thue-Morse inflation rule $f_{TM}(x)$ is given by:

A ⟶ AB
B ⟶ BA

Successive applications of the above inflation rule generate the one-dimensional Thue-Morse sequence, which is a non-periodic fractal sequence of two letters, A and B, without translational invariance. Some Thue-Morse sequence generations are explicitly shown below, starting from A as a seed letter:

A generation n=0
AB generation n=1
ABB generation n=2
ABBABAAB generation n=3
ABBABAABBAABABBA generation n=4
etc.

Now the 1D Thue-Morse sequence is extended to two dimensions. This is done by the definition of a square matrix obtained as:

$$f_{xy} = f_y(f_x(X))$$

where the Thue-Morse inflation is first applied in one direction starting from a seed letter X and successively inflating in the perpendicular direction each of the column elements.

Let the seed symbol be called A (represented as black box), and apply the Thue-Morse inflation $f_x$ from the first term A. This will result in the inflation of the term along the first direction, called the x direction, as follows:

First the inflation rule operates on the seed symbol A:
A becomes AB
After an inflation $f_y$ in the perpendicular direction, acting on each element of the previous sequence the following 2×2 matrix is obtained:

AB becomes AB
BA

To obtain the next generation of Thue-Morse matrices, the algorithm is repeated by an $f_x$ inflation of each row of the previously obtained matrix. This step will generate an intermediate 2×4 matrix. Upon the $f_y$ expansion of every element in each column of the intermediate matrix, the 4×4 Thue-Morse matrix corresponding to the third generation of the 2D generalized Thue-Morse is obtained.

By repeating successively the same algorithm we can obtain Thue-Morse square matrices of any order. FIG. 6 shows the first four generations. In general, the procedure described above is equivalent to the application of the following map:

$$A^{(1)} = A$$

$$A^{(n+1)}(x,y) = f_y \cdot (f_x(A^{(n)}))_{ij}$$

where · indicates the action of a the one dimensional $f_y$ Thue-Morse inflation on each column element of the intermediate matrix of dimension $2^{n-1} \times 2^n$, and n=1, 2, 3, . . . is the generation number.

Figure 7:
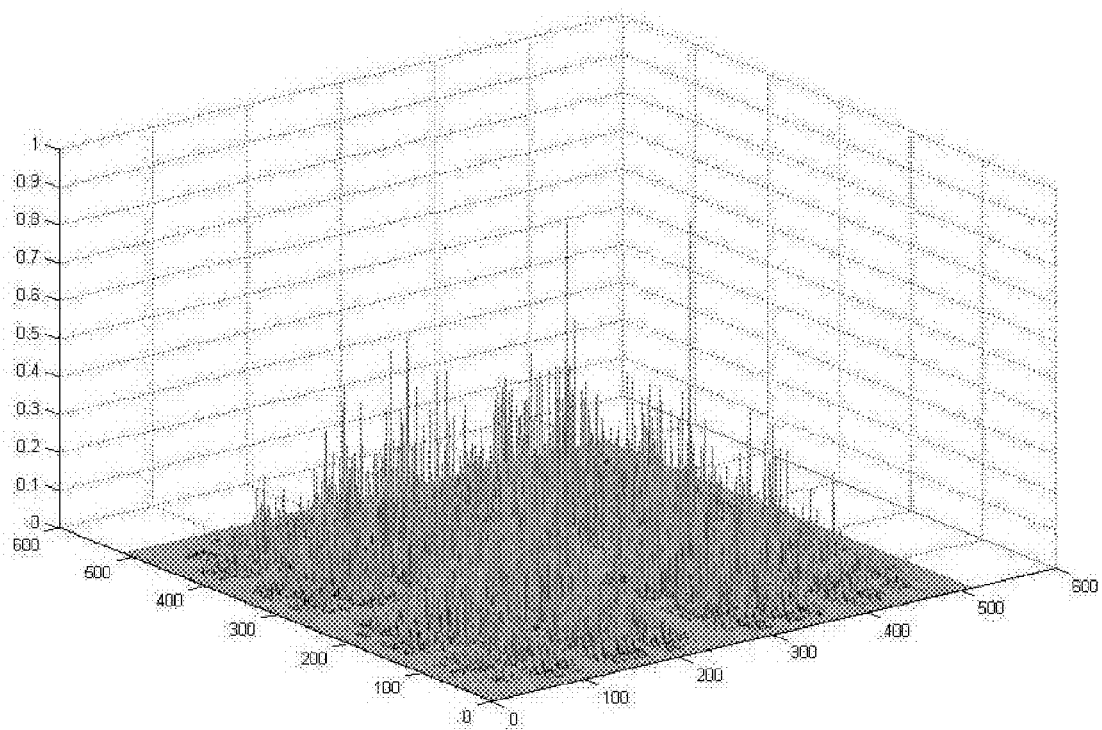
FIG. 7 is a plot of the two-dimensional spectrum of a TM device.
Figure 8:
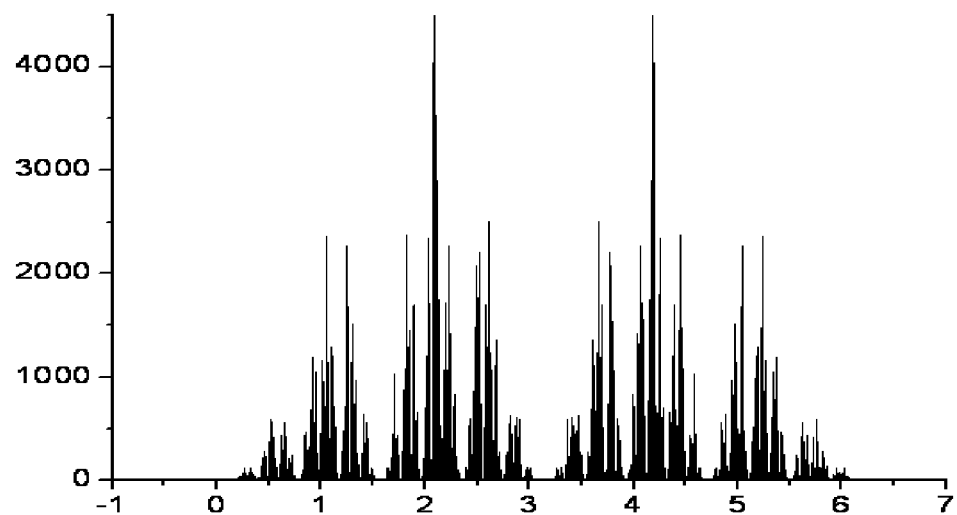
FIG. 8 is a plot of the spectrum of a one-dimensional TM sequence.
Figure 9:
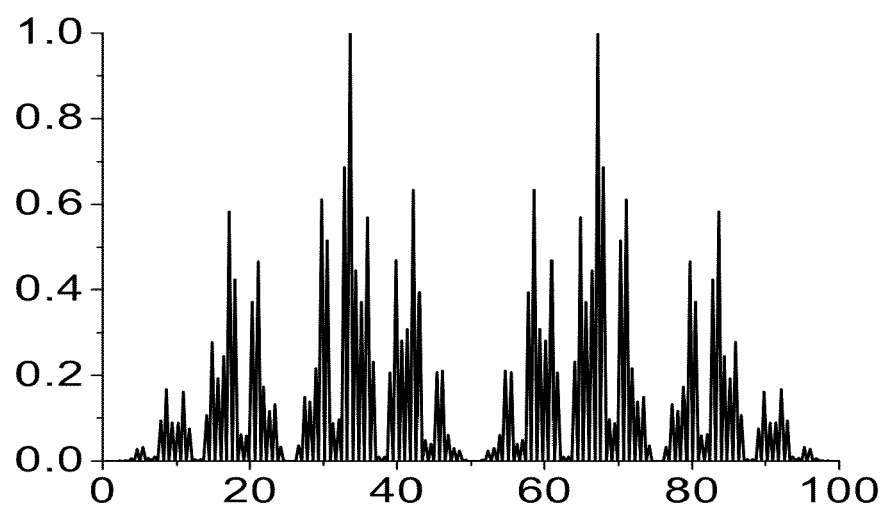
FIG. 9 is a plot of a single vertical slice of the two-dimensional spectrum of FIG. 7.

FIG. 7 shows the spectrum of the 2D Thue-Morse structure. For comparison purposes, FIGS. 8 and 9 show the comparison of the Fourier spectrum of a 1D Thue-Morse sequence (FIG. 8) with a slice of the 2D Fourier spectrum obtained from the extended Thue-Morse structure generated as described above (FIG. 9). The structure of the continuous 1D Thue-Morse Fourier spectrum is retained upon the two-dimensional generalization of the inflation rule.

It should be noted that the algorithm can be easily generalized to higher dimensions by following similar steps to those described above, given that a third spatial dimension and inflation $f_z$ are introduced.

Figure 10:
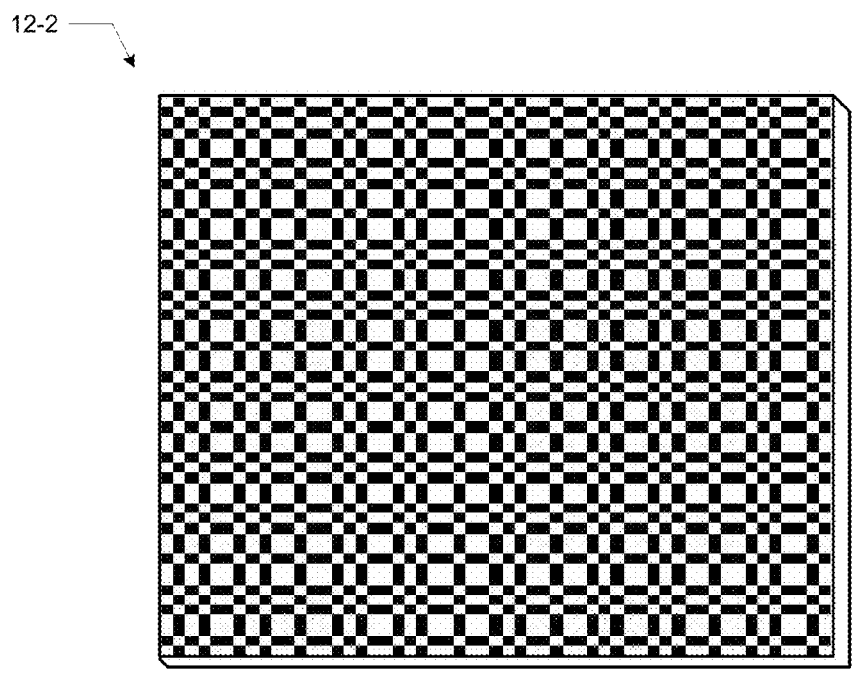
FIG. 10 is a diagram showing the patterning of a device according to a third embodiment based on a Fibonacci (Fib) sequence.

FIG. 10 shows a device 12-2 with patterning employing a 2D Fibonacci sequence based on the following 1D inflation rule $f_{fib}(x)$:

A ⟶ AB
B ⟶ A

The two-dimensional generalization of the Fibonacci sequence can be obtained by following a slightly modified algorithm with respect to the one described for the two previous sequences (Thue-Morse, RS). In particular, unlike the case of the previous two sequences, for Fibonacci the inflation is not alternated along the x and y dimensions. At each generation, two slightly different Fibonacci sequences $f_{fib}(x)$ and $f_{fib}(y)$ are generated, and a square matrix is created column by column as described below.

The principal steps of this method for the generalization of Fibonacci sequences are shown below. The two inflation rules to be used are:

$$f_{fib}(y) = A \longrightarrow AB$$

B ⟶ A, if the first term is A
B ⟶ BA
A ⟶ B, if the first term is B

The inflation rule $f_{fib}(y)$ for the second dimension makes sure that the sequence maintains its Fibonacci characteristic over the 2 spatial dimensions.

Figure 11:
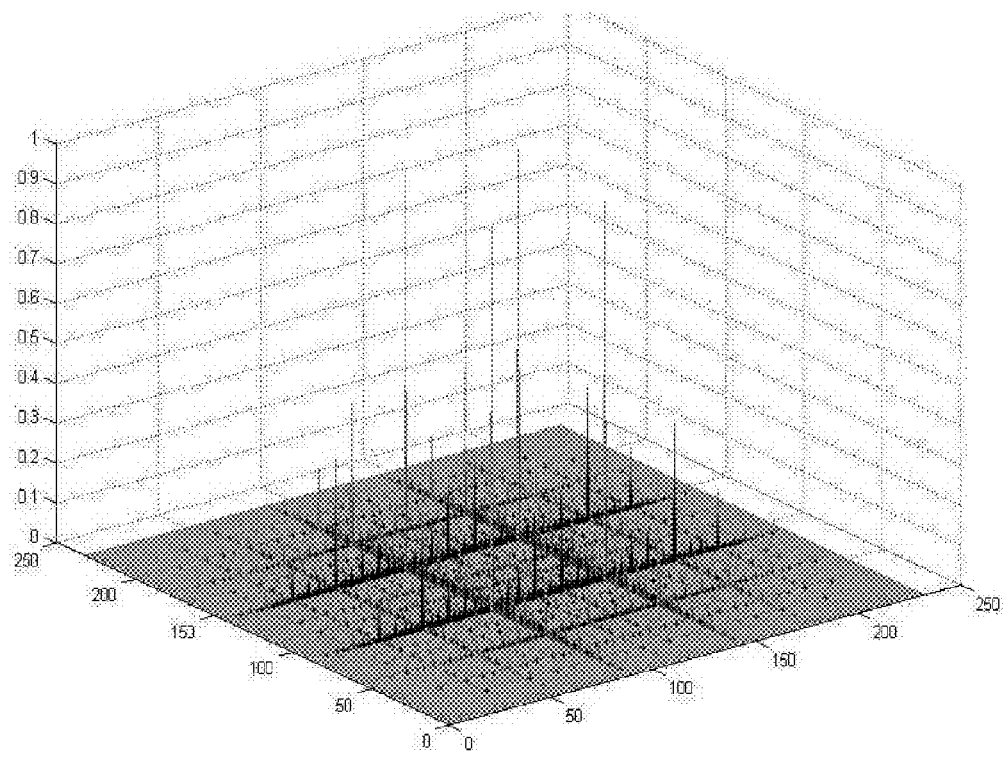
FIG. 11 is a plot of the two-dimensional spectrum of the Fib device of FIG. 10.
Figure 12:
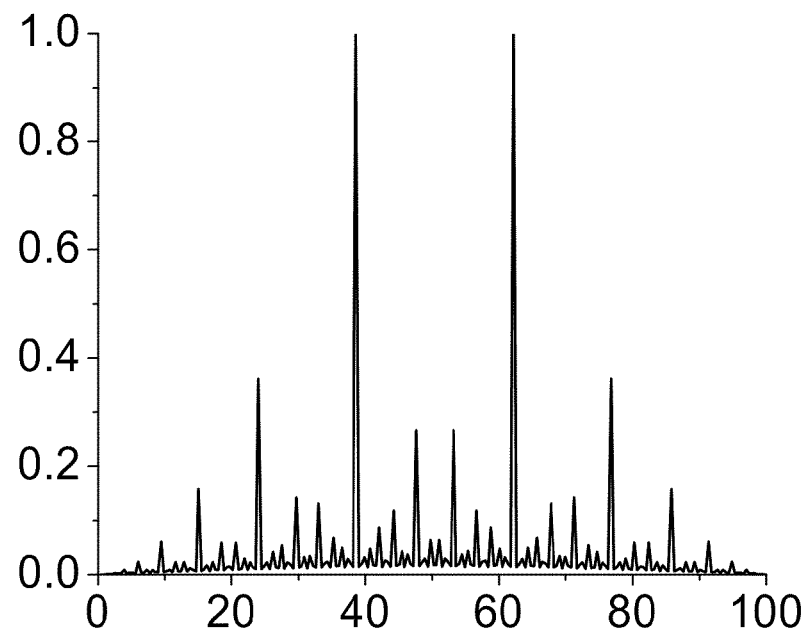
FIG. 12 is a plot of the spectrum of a one-dimensional Fib sequence.
Figure 13:
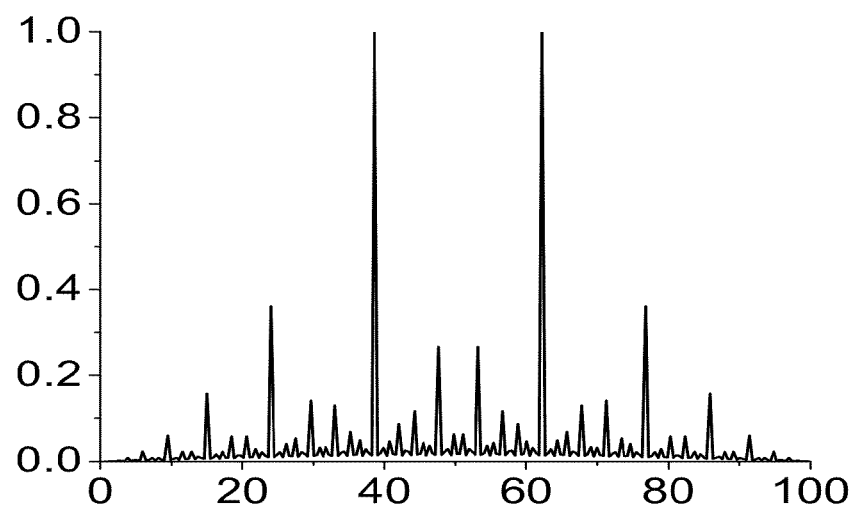
FIG. 13 is a plot of a single vertical slice of the two-dimensional spectrum of FIG. 11.

FIG. 11 shows the spectrum of the 2D Fibonacci sequence. For comparison purposes, FIG. 12 shows the spectrum of the 1D Fibonacci sequence, and FIG. 13 shows a 1D slice of the 2D spectrum of FIG. 11.

A brief description of plasmonic materials and the nature of plasmonic excitation is provided. Metal surfaces allow for the excitation of surface plasmon-polaritons (SPPs). SPPs are electromagnetic waves that propagate along a metal-dielectric interface and are coupled to the free electrons in the metal. These waves are transverse magnetic (TM) in nature. Their electromagnetic field intensity is highest at the surface and decays exponentially away from the interface. From an engineering standpoint a SPP can be viewed as a special type of light wave propagating along the metal surface. Metallic surfaces that support such waves thus serve as two-dimensional optical waveguides, termed plasmonic waveguides.

Patterns can be generated into a metal film by etching techniques or on top of the film by deposition techniques through the rules presented in the previous sections. Such patterns can give rise to strong SPP localization and confinement. The patterns can be both 1D (lines or grooves) or 2D (holes in any kind of several geometrical shape). Metallic surfaces lend themselves ideally to 1D and 2D structures to localize SPPs as they already naturally confine light in 1D dimension.

These types of nanopatterned metals are expected to show substantial field enhancements in certain regions close to the metal surface and combine easy coupling to SPP with SPP localization. Nanopatterned metal structures also enable localization and confinement of electromagnetic energy into deep subwavelength volumes.

Similar types of structures could be made in other polaritonic materials, such as for example SiC which supports surface phonon-polaritons. Semiconductors can be used as well at lower frequencies, at which they support SPPs.

The use of non-periodic, deterministic 1D and 2D metal nanoparticle arrays is important to the achievement of high electromagnetic localization (hot electromagnetic spots) with large field enhancement effects. These effects originate form strong multiple SPPs scattering in non-periodically patterned metal arrays and may not be achievable using periodic arrangements. The structures can be conveniently fabricated using standard techniques such as electron-beam lithography.

While various embodiments of the invention have been particularly shown and described, it will be understood by those skilled in the art that various changes in form and details may be made therein without departing from the spirit and scope of the invention as defined by the appended claims.

What is claimed is:

1. A device operative in response to incident electromagnetic energy to create a distribution of electromagnetic energy having localized electromagnetic field enhancement, the device comprising a dielectric or plasmonic material having a region of interaction with the incident electromagnetic energy, the region of interaction having a deterministic, aperiodic patterning with an array of individual patterning elements of distinct refractive indices such that a variation of refractive index of the device occurs over distances comparable or smaller with a wavelength of the incident electromagnetic energy, the array being a multi-dimensional extension of a corresponding one-dimensional sequence such that a spectral response of the array is a multi-dimensional equivalent of a spectral response of the one-dimensional sequence.

2. A device according to claim 1, wherein the array is a multi-dimensional extension of a Rudin-Shapiro sequence.

3. A device according to claim 1, wherein the array is a multi-dimensional extension of a Thue-Morse sequence.

4. A device according to claim 1, wherein the array is a multi-dimensional extension of a Fibonacci sequence.

5. A device according to claim 1, wherein the region of interaction is a surface of the device and the array is a two-dimensional array.

6. A device according to claim 1, wherein the region of interaction is a volume of the device and array is a three-dimensional array.

7. A device according to claim 1, wherein the patterning elements comprise discrete particles distinct from a substrate material in the region of interaction.

8. A device according to claim 7, wherein the particles comprise metallic nanoparticles.

9. A device according to claim 1, wherein the patterning elements comprise patterned features formed in a substrate material in the region of interaction.

10. A device according to claim 9, wherein the patterned features comprise holes formed in the substrate material.

11. A device according to claim 1, configured as a support device for a selected one of surface-enhanced Raman spectroscopy and single-molecule detection.

* * * * *